United States Patent
Sharkey et al.

(10) Patent No.: US 9,233,005 B2
(45) Date of Patent: *Jan. 12, 2016

(54) SUBCHONDRAL TREATMENT OF JOINT PAIN OF THE SPINE

(71) Applicant: ZIMMER KNEE CREATIONS, INC., Exton, PA (US)

(72) Inventors: Peter F. Sharkey, Villanova, PA (US); Charles F. Leinberry, Chester Springs, PA (US); David L. Nichols, West Chester, PA (US); Marc R. Viscogliosi, New York, NY (US); Hallett Mathews, Williamsburg, VA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,098

(22) Filed: Mar. 18, 2015

(65) Prior Publication Data
US 2015/0190238 A1 Jul. 9, 2015

Related U.S. Application Data

(63) Continuation of application No. 14/565,845, filed on Dec. 10, 2014, now Pat. No. 9,101,481, which is a continuation of application No. 14/149,406, filed on Jan. 7, 2014, now Pat. No. 8,911,481, which is a continuation of application No. 13/568,549, filed on Aug. 7, 2012, now Pat. No. 8,623,089.

(60) Provisional application No. 61/515,961, filed on Aug. 7, 2011.

(51) Int. Cl.
*A61B 17/70* (2006.01)
*A61F 2/44* (2006.01)
(Continued)

(52) U.S. Cl.
CPC . *A61F 2/44* (2013.01); *A61B 17/56* (2013.01); *A61B 17/70* (2013.01); *A61F 2/442* (2013.01); *A61F 2/4611* (2013.01); *A61L 27/50* (2013.01); *A61B 2017/564* (2013.01); *A61F 2002/30013* (2013.01); *A61F 2002/30034* (2013.01); *A61F 2002/30092* (2013.01); *A61F 2002/3098* (2013.01); *A61F 2002/30153* (2013.01); *A61F 2002/30224* (2013.01); *A61F 2002/30261* (2013.01); *A61F 2002/30263* (2013.01); *A61F 2002/30275* (2013.01); *A61F 2002/30281* (2013.01);
(Continued)

(58) Field of Classification Search
None
See application file for complete search history.

(56) References Cited

U.S. PATENT DOCUMENTS

| 5,514,137 A | 5/1996 | Coutts |
| 5,556,429 A | 9/1996 | Felt |

(Continued)

OTHER PUBLICATIONS

"U.S. Appl. No. 13/568,549, Notice of Allowance mailed Oct. 29, 2013", 14 pgs.
(Continued)

*Primary Examiner* — David H Willse
*Assistant Examiner* — Javier Blanco
(74) *Attorney, Agent, or Firm* — Schwegman Lundberg & Woessner, P.A.

(57) ABSTRACT

Methods for altering the natural history of degenerative disc disease and osteoarthritis of the spine are proposed. The methods focus on the prevention, or delayed onset or progression of, subchondral defects such as bone marrow edema or bone marrow lesion, and subchondral treatment to prevent the progression of osteoarthritis or degenerative disc disease in the spine and thereby treat pain.

14 Claims, 1 Drawing Sheet

(51) Int. Cl.
   *A61F 2/46* (2006.01)
   *A61B 17/56* (2006.01)
   *A61L 27/50* (2006.01)
   *A61F 2/30* (2006.01)

(52) U.S. Cl.
   CPC ............ *A61F 2002/30454* (2013.01); *A61F 2002/30601* (2013.01); *A61F 2002/30906* (2013.01); *A61F 2002/30925* (2013.01); *A61F2002/30927* (2013.01); *A61F 2002/4475* (2013.01); *A61F 2310/00017* (2013.01); *A61F 2310/00023* (2013.01); *A61F 2310/00029* (2013.01); *A61F 2310/00131* (2013.01); *A61F 2310/00407* (2013.01); *A61F 2310/00598* (2013.01); *A61L 2400/06* (2013.01); *A61L 2430/38* (2013.01)

(56) References Cited

U.S. PATENT DOCUMENTS

| | | | |
|---|---|---|---|
| 5,755,809 | A | 5/1998 | Cohen et al. |
| 6,140,452 | A | 10/2000 | Felt et al. |
| 6,235,043 | B1 | 5/2001 | Reiley et al. |
| 6,241,734 | B1 | 6/2001 | Scribner et al. |
| 6,248,110 | B1 | 6/2001 | Reiley et al. |
| 6,306,177 | B1 | 10/2001 | Felt et al. |
| 6,395,007 | B1 | 5/2002 | Bhatnagar et al. |
| 6,564,083 | B2 | 5/2003 | Stevens |
| 6,607,561 | B2 | 8/2003 | Brannon |
| 6,613,054 | B2 | 9/2003 | Scribner et al. |
| 6,719,761 | B1 | 4/2004 | Reiley et al. |
| 6,746,451 | B2 | 6/2004 | Middleton et al. |
| 6,827,720 | B2 | 12/2004 | Leali |
| 6,863,899 | B2 | 3/2005 | Koblish et al. |
| 6,887,246 | B2 | 5/2005 | Bhatnagar et al. |
| 7,153,307 | B2 | 12/2006 | Scribner |
| 7,261,720 | B2 | 8/2007 | Stevens et al. |
| 7,708,742 | B2 | 5/2010 | Scribner et al. |
| 7,771,431 | B2 | 8/2010 | Scribner et al. |
| 7,811,290 | B2 | 10/2010 | Rabiner |
| 8,152,813 | B2 | 4/2012 | Osorio et al. |
| 8,168,692 | B2 | 5/2012 | Wenz |
| 8,623,089 | B2 | 1/2014 | Sharkey |
| 8,911,481 | B2 | 12/2014 | Sharkey et al. |
| 2003/0138473 | A1 | 7/2003 | Koblish et al. |
| 2005/0119219 | A1 | 6/2005 | Bellini et al. |
| 2006/0064164 | A1 | 3/2006 | Thelen et al. |
| 2010/0076503 | A1 | 3/2010 | Beyar et al. |
| 2010/0179549 | A1 | 7/2010 | Keller et al. |
| 2011/0125157 | A1 | 5/2011 | Sharkey et al. |
| 2011/0125264 | A1 | 5/2011 | Bagga et al. |
| 2011/0125265 | A1 | 5/2011 | Bagga et al. |
| 2011/0125272 | A1 | 5/2011 | Bagga et al. |
| 2013/0035761 | A1 | 2/2013 | Sharkey et al. |
| 2014/0121708 | A1 | 5/2014 | Sharkey et al. |

OTHER PUBLICATIONS

"U.S. Appl. No. 14/149,406, Notice of Allowance mailed Aug. 15, 2014", 12 pgs.

"U.S. Appl. No. 14/149,406, Preliminary Amendment filed May 13, 2014", 5 pgs.

"U.S. Appl. No. 14/565,845, Preliminary Amendment filed Dec. 11, 2014", 5 pgs.

"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.

"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.

"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

Rahme, et al., "The Modic Vertebral Endplate and Marrow Changes: Pathologic Significance and Relation to Low Back Pain and Segmental Instability of the Lumbar Spine", AJNR 29, (May 2008), 5 pgs.

SUBCHONDRAL TREATMENT OF JOINT PAIN OF THE SPINE

CROSS-REFERENCE TO RELATED APPLICATIONS

This application is a continuation of U.S. patent application Ser. No. 14/565,845 filed Dec. 10, 2014, which is a continuation of U.S. patent application Ser. No. 14/149,406 filed Jan. 7, 2014, now issued as U.S. Pat. No. 8,911,481, which is a continuation of U.S. patent application Ser. No. 13/568,549 filed Aug. 7, 2012 and entitled "Subchondral Treatment of Joint Pain of the Spine," now issued as U.S. Pat. No. 8,623,089, which application claims priority to U.S. Provisional No. 61/515,961 filed Aug. 7, 2011 and entitled "Subchondral Treatment of Joint Pain of the Spine," the contents of which are incorporated by reference in their entirety.

FIELD

The present invention relates to methods for treating joint pain of the spine. More particularly, the present invention relates to methods to prevent the progression of degenerative disc disease or osteoarthritis of the spine by treating the subchondral bone of the vertebral body of the spinal segment.

BACKGROUND

Human joints are susceptible to degeneration from disease, trauma, and long-term repetitive use that eventually lead to pain. In the spine, degenerative spine disease is a major cause of chronic disability in the adult working population. Spinal degeneration is a normal part of aging, and neck and back pain are one of life's most common infirmities.

There are many potential sources of back pain, and finding the specific cause is often a confounding problem for both patient and doctor. Pain can originate from bone, joints, ligaments, muscles, nerves and intervertebral disks, as well as other paravertebral tissues. For acute pain due to structural damage of the spine, treatments that repair the damaged area, such as by mechanical fixation devices like fixation plates or rods, have proven effective. These treatments generally involve the immobilization of the damaged area through spine restabilization, thus altering the load sharing of each segment. This is commonly performed by in situ, on lay, interbody, and other fusion procedures that improve loading of the diseased subchondral defects (e.g., edema or lesions), and load transfer to other areas and implantable devices. When fusion is not desirable, implantable motion preservation devices may accomplish this load transfer and improve stability while reducing pain.

Unlike acute injuries or trauma of the spine, current treatments for chronic back pain due to degenerative disc disease or osteoarthritis have not proven as reliable or effective. Many medical practitioners focus treatment on the intervertebral disc, because they have attributed disc degeneration, more specifically the initial delamination of the annulus, followed by nucleus dehydration and subchondral bone changes, as a continuum of events as the degenerative disease cascade progresses. Current treatments comprise, for example, partial or complete fusion to immobilize and/or isolate the damaged area, intervertebral disc repair or replacement, nucleus repair or replacement, and corpectomy.

The rationale for treating the disc as a pain source in the spine is similar to the popular theory within the orthopedic community that joint pain, such as that found in the knee or hip, results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. However, the severity of osteoarthritis, especially in the knee, has been found to correlate poorly with the incidence and magnitude of knee pain. Because of this, surgeons and medical practitioners have struggled to deliver consistent, reliable pain relief to patients, especially if preservation of the joint is desired. Likewise, in the spine, practitioners have not found long-term results from chronic back pain by treating the intervertebral disc as the source and solution of mechanical loading pain of a diseased spinal segment.

Accordingly, it would be desirable to provide a medical procedure that addresses the pain associated with degenerative disc disease or osteoarthritis of the spine, and provides an alternative to a fusion or replacement surgery, which can be highly invasive, risky and irreversible.

SUMMARY

The present disclosure provides methods for the treatment of pain of the spine due to osteoarthritis (OA) or degenerative disc disease (DDD). The methods involve treating the subchondral bone to prevent the manifestation of, delay the onset or progression of, or repair any existing, bone marrow edema or lesion in the subchondral space.

In one embodiment, a method for treating joint pain of the spine is provided. The method comprises: identifying a subchondral defect in a subchondral region of a bone of the spine; selecting a subchondral access path to a location near the subchondral defect; and treating the subchondral defect, via the subchondral access, in a manner that reduces or relieves pain. The subchondral defect may be a bone marrow lesion or bone marrow edema, and can further include sclerotic bone or a fracture. The treatment may comprise mechanically stabilizing the defect, or stimulating a healing response to heal the defect or improve nutrition to the nucleus. The access path may be achieved through, for example, open approaches, transpedicular, and Craig needle biopsy approaches to access the vertebral body. The subchondral defect may be identified with MRI, x-ray, or any validated diagnostic modality that can identify bone, soft tissue, and fluid interfaces, including ultrasound and injectable labeled and radionucleotide tagged materials that may expose and display these defects sufficiently to differentiate active vs. chronic defects and healing response.

In another embodiment, a method for treating joint pain of the spine is provided. The method comprises: identifying a subchondral defect in a subchondral region of a bone of the spine; selecting a subchondral access path to a location near the subchondral defect; and treating the subchondral defect, via the subchondral access, by mechanically stabilizing an area in or near the subchondral defect; wherein treatment of the subchondral defect reduces or relieves pain. The treatment may comprise implanting an implant sufficient to alter forces applied on the subchondral defect. The treatment may also include injecting a bone hardening material such as bone cement, bone void filler, or bone substitute material. The access path may be achieved through, for example, open approaches, transpedicular, and Craig needle biopsy approaches to access the vertebral body.

In yet another embodiment, a method for treating joint pain of the spine is provided. The method comprises: identifying a subchondral defect in a subchondral region of a bone of the spine; selecting a subchondral access path to a location near the subchondral defect; and treating the subchondral defect, via the subchondral access, by stimulating healing of the bone tissue in or adjacent to the subchondral defect; wherein treatment of the subchondral defect reduces or relieves pain. Healing may be stimulated by drilling into the bone tissue via the access path, applying electrical or heat stimulation, applying biological or chemical stimulation, or injecting a bone growth inducing material, including allograft, autograft, bone void fillers and BMP to be used alone or with implantable structural devices. The access path may be achieved through, for example, open approaches, transpedicular, and Craig needle biopsy approaches to access the vertebral body.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1:
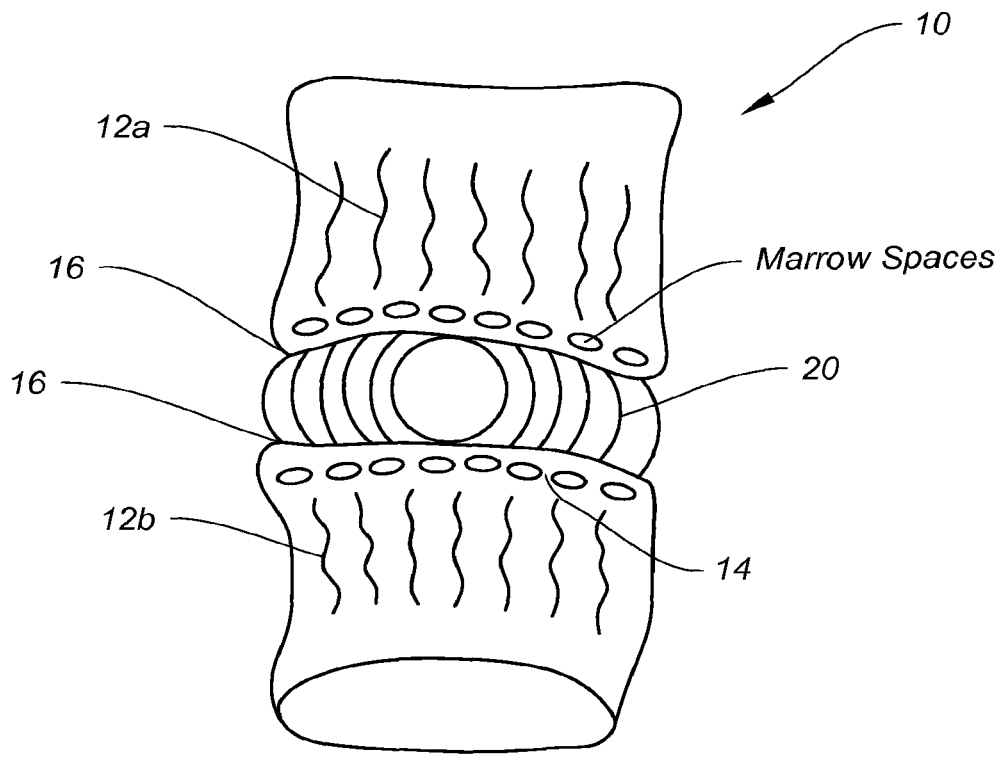
FIG. 1 shows an exemplary functional spinal unit including its major components.

Methods for altering the natural history of degenerative disc disease and osteoarthritis of the spine are proposed. These methods aim to prevent, alter, therapeutically treat, and lessen structural spine pain associated with subchondral defects such as edema or lesions near and around the cartilaginous endplate of the vertebral body and/or both facets of each spinal segment. It is believed that the treatment of these subchondral defects beneath the diseased disc segments improves disc loading, nutrient transfer through the subchondral plate, and relieves pain while allowing the disc to stabilize and improve its natural function. Ultimately, these methods address the problem of chronic back pain, and provide a more consistent and reliable alternative to surgical procedures like intervertebral disc replacement, nucleus replacement, annulus repair, interbody fusions, with or without implanted devices, or rod-based pedicle screw system implantation.

As previously mentioned, most current treatments for back pain focus on the disc, particularly the annulus and nucleus for the source of the failing spinal segment with pain. Yet practitioners have not found long-term results from chronic back pain by treating the intervertebral disc as the source and solution of mechanical loading pain of a diseased spinal segment. Diagnostic tests such as MRI have helped identify degenerative disc segments including changes in the annulus, nucleus, endplate, and subchondral bone. Other tests, such as discography, have lacked specificity and sensitivity to predictably correlate the source of pain with degenerative spine loading pain. Discography has been shown to advance the degeneration of the affected and tested disc when normal levels were tested. Studies showing complete fusion of degenerative segments do not always correlate with predictable pain relief. Furthermore, subchondral defects like edema or lesions may still exist on MRI even after solid fusion of motion segments. Until now, methods for treating pain have not focused on the supporting and nutrient transferring subchondral bone beneath the disc space.

A technique, SUBCHONDROPLASTY™ or SCP™, for repairing damaged subchondral bone associated with joint OA has previously been described in U.S. application Ser. No. 12/950,355. SCP™ has proven to predictably relieve knee OA pain and improve patient reported quality of life. SCP™ is a unique intervention allowing for the repair of damaged subchondral bone without violating the articular surface of the joint. Resolution of BME has been shown to slow knee OA progression. That the theory behind the identification of bone marrow edema (BME) or bone marrow lesion (BML) as the pain generator in OA and subsequent treatment of the BME/BML in subchondral bone to alleviate pain applies equally to the spine.

MRI changes of the vertebral body in DDD patients with no correlation to osteoporosis has previously been reported. Most clinicians believed that the annulus, and later the nucleus, were the causes of defects (edema/lesion) in the subchondral bone, and therefore treating the annulus and disc would relieve pain. In fact, these modic changes, which are prevalent in patients with DDD, may be the root cause of pain. And until now, the focus of treatments has not correlated the subchondral defects identified as the reactive structure and source of pain.

As noted, embodiments of the present disclosure may be explained and illustrated with reference to treatment of a patient's spine. Referring now to FIG. 1, a healthy spinal segment, or functional spinal unit, 10 comprising a superior vertebral body 12a and inferior vertebral body 12b is shown. The vertebral bodies 12a, 12b comprise endplates 16 which abut an intervertebral disc 20 that resides between the vertebral bodies 12a, 12b. As shown in FIG. 1, marrow spaces are located below the vertebral endplates 16 in the subchondral bone 14 of each of the vertebral bodies 12a, 12b.

Figure 2:
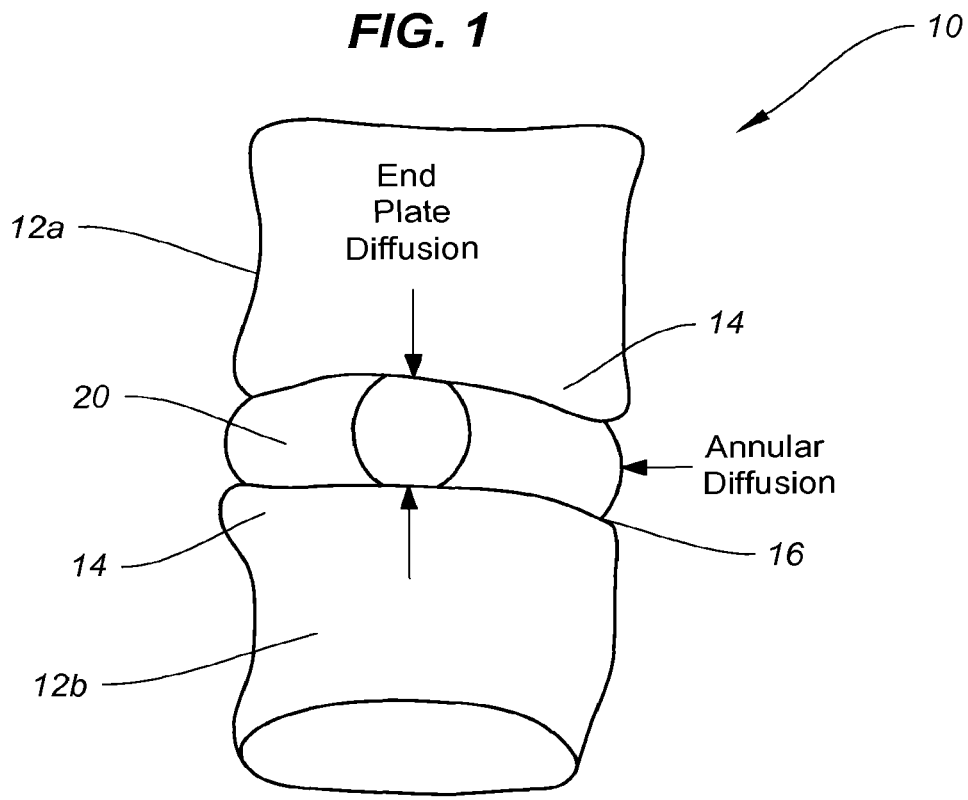
FIG. 2 illustrates the perfusion dynamics of the functional spinal unit of FIG. 1.

In a healthy spine, the intervertebral disc 20 receives nutrients by way of diffusion through the cartilaginous vertebral endplates 16. This nutrient flow dynamic, as represented by the arrows in FIG. 2, suggests that endplate 16 integrity plays a crucial role in the health of the disc 20 itself. The presence of a diseased or damaged disc 20 may suggest the lack of nutrients flowing to the disc 20 due to an unhealthy endplate 16. Moreover, these modic changes (changes to the vertebral body) may manifest due to the presence of BME/BML in the subchondral bone of the vertebral body. Previous studies have already correlated modic vertebral endplate degeneration and vertebral marrow edema with a decrease in nutrient diffusion to the disc. Similar to the cartilage damage seen in knee joints where a stressed fracture or non-union in the subchondral bone turns into a BME over time, in the vertebral body a fracture beneath the subchondral plate or non-union under stress and unable to heal itself through the body's natural reparative process through Wolfe's Law may manifest into BME/BML in the subchondral space. Hardened sclerotic bone may also be present, such as in the endplates 16. Such hardening may represent a chronic attempt to heal the subchondral defect, as well as a path to osteonecrosis or avascularnecrosis (AVN), as seen in the hip, knee, talus, and other bones. This type of subchondral defect (BME/BML), along with sclerotic hardening, occurs when the force on the initial fracture exceeds remodeling conditions (i.e., Wolfe's Law is rendered ineffective) and is particularly prevalent in weight bearing joints.

In this scenario where the BME/BML becomes chronic and does not heal, pain is generated. The intervertebral disc 20 may be dying due to lack of nutrition from the sclerotic endplates 16. When the practitioner sees the narrowing of the disc space and the general damage to the disc 20, the current tendency is to treat the disc 20 to relieve pain. However, the present disclosure proposes treating the subchondral bone to restore the normal joint function to treat the pain with the SCP™ techniques disclosed, since the perceived pain is actually generated from the underlying BME/BML in the subchondral bone and the cascade of resulting damage that this creates, rather than the disc 20.

The SCP methods employ one or more treatment modalities to address the subchondral bone. By subchondral bone, what is meant is any bone that exists beneath calcifying matrix in the tidemark zone of hyaline articular cartilage. This includes the cartilaginous endplate and the diffusion channels that originate and traverse through the subchondral space, through the endplate, into the nucleus.

In one treatment modality, the subchondral bone can be strengthened by the introduction of a hardening material, such as a bone substitute, in the localized region. In another treatment modality, the subchondral bone can be stimulated to trigger or improve the body's natural healing process, optionally with the use of bone grafts, osteoinductive and osteoconductive materials including bone morphogenic protein (BMP). In yet another treatment modality, an implantable device may be implanted into the localized region of the subchondral bone to provide mechanical support to the localized bone region.

The current proposed methods apply the SCP™ techniques to the spine to treat chronic pain from degenerative disc disease (DDD) or osteoarthritis (OA). The methods are intended to prevent the manifestation of any bone marrow edema or bone marrow lesion in the subchondral bone, which as previously described is one of the underlying root causes for joint pain and the progression of DDD or OA in a joint. These methods involve accessing, repairing, enhancing, and/or stimulating subchondral bone in the vertebral bodies. These methods prevent bone marrow edema or bone marrow lesions from manifesting in subchondral bone, ultimately treating the DDD and OA itself by preventing or delaying the disease progression.

The embodiments treat the subchondral region of a spine to prevent bone marrow edema and treat osteoarthritis or degenerative disc disease by inhibiting its progression. As previously mentioned, the methods disclosed are based upon the theory that back pain associated with OA or DDD can be correlated to bone defects or changes at the subchondral level rather than, for example, the severity of damage to the disc, including more specifically, the annulus, nucleus and the subchondral plate. In particular, bone defects, such as bone marrow lesions, edema, fissures, fractures, hardened bone, etc. near the joint surface lead to a mechanical disadvantage and abnormal stress distribution in the subchondral bone, which may cause inflammation and generate pain. By subchondral bone, what is meant is any bone that exists beneath calcifying matrix in the tidemark zone of hyaline articular cartilage. This includes the cartilaginous endplate and the diffusion channels that originate and traverse through the subchondral space, through the endplate, into the nucleus. By altering the makeup of the subchondral bone (which may or may not be sclerotic) in relation to the surrounding region, it is possible to change the structural integrity of the affected bone and restore normal subchondral force transmission and/or stimulate bone repair, thus leading to a delay or prevention of DDD/OA symptoms and/or DDD/OA progression.

Treatment of the bone by mechanical and/or biological means to restore the normal physiologic stress distribution, and restore the healing balance of the bone tissue at the subchondral level, is a more effective way of treating pain than conventional techniques. That is, the treatment can be effectively achieved by: (a) mechanically strengthening or stabilizing the subchondral bone; (b) biologically initiating or stimulating a healing response in the subchondral bone to a stressed defect, such as, for example, an impending or actual stress fracture; or (c) both (a) and (b) combined. Accordingly, the present disclosure provides methods for a subchondral procedure.

The subchondral techniques disclosed herein apply previously described SCP™ methods to prevent or delay the progression of OA or DDD in the spine. These methods endeavor to treat the subchondral bone by: (a) mechanically strengthening or stabilizing the subchondral bone; (b) biologically initiating or stimulating a healing response in the subchondral bone; or (c) both (a) and (b) combined. By doing so, SCP aims to prevent the manifestation of BME's and other subchondral defects in the subchondral bone, which defects can lead to the progression of the OA/DDD and eventual increased pain and decreased joint function. Further, these methods alter the natural progressive history of OA and DDD, preventing subchondral bone forces from continually increasing by inhibiting the disease progression.

In general, these methods are similar to the SUBCHONDROPLASTY™, or SCP™, techniques and are intended to both strengthen the bone and stimulate the bone. As with SCP, bone fractures or non-unions are stabilized, integrated or healed, which results in repair and/or resolution of a bone defect, such as a bone marrow lesion or edema. In addition, the methods restore or alter the distribution of forces in the spine to thereby relieve pain. These methods can be performed arthroscopically or percutaneously to treat a stressed fracture, preventing the manifestation of any bone marrow lesion or edema during the progression of the OA or DDD, and avoiding or delaying the need for more risky, irreversible surgeries.

The present disclosure provides several exemplary treatment modalities for the different extents of treatment needed. Accordingly, a medical practitioner may elect to use any of the techniques and devices described herein, either alone or in combination, to subchondrally treat the subchondral bone as he or she deems appropriate.

The present methods provide a number of treatment modalities for treating the subchondral bone. These treatment modalities may be used alone or in combination. The ultimate goal of these modalities is to restore mechanical stability to the subchondral bone of the vertebral body 12a, 12b of the functional spinal unit 10. In untreated subchondral bone, an already stressed defect, such as an impending or actual stress fracture, becomes aggravated as the disease progresses and results in the formation of other, more severe defects like BME's. The present methods aim to prevent the manifestation of BME's and other subchondral defects in the subchondral bone, which defects can lead to the progression of the OA/DDD and eventual increased pain and decreased joint function. Further, these methods alter the natural progressive history of OA and DDD, preventing subchondral bone forces from continually increasing by inhibiting the disease progression.

In one treatment modality, the subchondral bone of the vertebral body can be strengthened by the introduction of a hardening material, such as a bone substitute, in the localized region. In some instances, some of the soft bone tissue in the localized region of the subchondral bone is compacted prior to insertion of the hardening material. The bone substitute may be an injectable calcium phosphate ensconced in an optimized carrier material. In some cases, the injected material may also serve as a bone stimulator that reinvigorates the bone's natural repair and healing activity. Treatments may include, for example, treating acid/base imbalances, treatments targeting specific neurotransmitters known to be present during painful inflammation, and those proteins that may be specifically biopsied or assayed in these defects, thus leading to a specific therapy designed for that defect as a treatment, device, or injectable therapeutic.

For example, polymethylmethacrylate (PMMA) or calcium phosphate (CaP) cement injections can be made at the subchondral localized region. PMMA injection may increase the mechanical strength of the bone, allowing it to withstand greater mechanical stresses. CaP cement injection may also increase the mechanical strength of the bone, while also stimulating the localized region for bone fracture repair.

Suitable treatment or hardening materials include but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber, polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

In some embodiments, the material may be of a type that can expand upon insertion. For example, the material may be injectable at the localized region of the subchondral bone, whereupon it can fill up or expand into the region. If desired, the material may also be implanted in a step-wise fashion such that an initial stage to establish primary fixation is followed with a subsequent stage of assembly that provides added strength and bone integration properties to the fully assembled material.

In another treatment modality, the subchondral bone of the vertebral body can be stimulated to trigger or improve the body's natural healing process. For example, in one embodiment of this treatment modality, small holes may be drilled at the localized region of the subchondral bone to increase stimulation (e.g., blood flow, cellular turnover, etc.) and initiate bone repair. In another embodiment, after holes are drilled an osteogenic, osteoinductive, or osteoconductive agent may be introduced to the localized region of the subchondral bone. In addition, some of the bone tissue may be compacted in order to assist in stimulating the bone tissue or create space for the introduction of bone graft material. Bone graft material, for example, may be used to fill the hole. This treatment modality may create a better load-supporting environment leading to long term healing. Electrical or heat stimulation may also be employed to stimulate the healing process of a chronically injured bone, as well as for energy induced denaturation of local nerves in and around the subchondral defects. Chemical and bio-chemical stimulation may also be employed, including other mechanisms for generating a response that may favorably alter the degenerative pathway and response to pain. Moreover, stimulation of bone tissue may be enhanced via the use of cytokines and other cell signaling agents to trigger osteogenesis, chondrogenesis, and/or angiogenesis to perhaps reverse the progression of osteoarthritis.

In yet another treatment modality, one or more implantable devices, depending on the size of the area to be treated, may be implanted into the localized region of the subchondral bone of the vertebral body to provide mechanical support to the localized bone region, particularly where an insufficiency fracture or stress fracture is present. In some embodiments, some of the bone tissue may be compacted in order to create space for the implantable device. The implant may help create a better load distribution in the subchondral region. In addition, the implant may mechanically integrate with the surrounding healthy bone tissue.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected localized bone region. In addition, the implant may also serve as a portal to inject the augmentation material into the subchondral bone region.

As noted, the methods described herein may provide various treatment modalities and employ different types of implantable devices. The may have various forms and shapes to maximize its surface area and reduce stress of the bone when implanted. For example, the implantable device may be in the form of a rod having a triangular profile, a rectangular profile, or a circular profile. The implantable device may be planar, e.g., relatively long in two dimensions and relatively short in a third dimension. Planar implantable devices in accordance with the invention can have a thickness which is ≤50% of the length and ≤50% of the width of a rectangular implantable device (or ≤50% of the diameter in the case of a circular implantable device or ≤50% of the height and ≤50% of the base in the case of a triangular implantable device).

In other embodiments, the implantable device may have a wedge-shaped edge on at least one edge or a wedge or ramp shape when viewed from the side. A wedge-shaped edge may be adapted to facilitate inserting the implantable device into the bone. Thus, the particular angle and other dimensions of the wedge may be dictated by factors that are known in the art. As a wedge-shaped implant, the implantable device may be similar to standard surgical tools, such as osteotomes, or comprise blade plates or osteotomy staples. Further, the implantable device may be an expandable device that can span the targeted localized region. In one embodiment, the implantable device may be an expandable screw, such as an osseoscrew.

In other embodiments, the implantable device may be in the form of a closed disc, an open disc, a screw-shaped device, or an elongated pin. In addition, the implantable device may have a square profile, rectangular profile with rounded edges, or an I-beam profile. Alternatively, the implantable device can be an injection cement diffuser. In some embodiments, the implantable device may be approximately 3 mm thick.

In some embodiments, the implantable device may be customized to the patient. For example, using 3-dimensional imaging technology, it may be desirable to provide an implant that matches precisely the anatomical localized region of the subchondral bone where the implantable device is to be placed. This would ensure conformability and avoid a less than perfect match between the implant and the targeted localized region of the subchondral bone.

The implantable device may be porous and/or fenestrated to allow for bone ingrowth. Implantable device comprises a physiologically compatible material that has sufficient durability to reinforce the overstressed bone of the bone lesion and bear physiologic loads. Materials for the implantable device can include metals, such as titanium, stainless steel, alloys of cobalt and chrome, tantalum, alloys of titanium and nickel and other superelastic metal alloys. Porous, titanium, titanium "foam", tantalum, trabecular metals, nanoceramics, porous nitinol, or other highly porous nanomaterials, and chrome cobalt may also be employed in the implantable device.

The implantable device may comprise a functional coating, such as, hydroxyapatite plasma coating, titanium nitrate or bioactive glass. In addition, the implantable device may undergo some form of surface treatment including acid etching, grit blast, or plasma spray. The implantable device may also comprise structural enhancements such as meshes, and include autograft. The implantable device may also be formed of, or include, porous metals like tantalum or ACTIPORE.

Other embodiments comprise the use of bone, such as autografts, allografts, and artificial or synthetic bone substitutes. Certain embodiments comprise the use of polymeric materials. A combination of materials, such as a porous metal applied to a carbon fiber implant may be employed in the implantable device.

The implantable device can be osteogenic, osteoconductive, and/or osteoinductive. Osteoconductive materials that may be used include but are not limited to collagen and the various forms of calcium phosphates including hydroxyapatite, tricalcium phosphate, and fluoroapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. Bone marrow, blood plasma, or morselized bone of the patient, or commercially available materials may also be used.

The implantable device may be treated prior to implantation. For example, the implantable device may be dipped or coated with bone conductive or bone inductive material. Osteoinductive materials, such as BMP, may be applied to, for example, by immersing the implantable device in an aqueous solution of this material in a dilute suspension of type I collagen. Osteoinductive materials such as TGF-beta may be applied from a saline solution containing an effective concentration of TGF-beta, or may be carried in the resilient material. Of course, other biologics may be applied by any method known in the art.

The implantable device can be resorbable or non-resorbable. For example, the implantable device may comprise PEEK, PGA, or PLA material. Electrical stimulation can also be applied to the bone to promote bone healing. The implantable device may also be capable of imbibing bone stimulating material, such as porous nitinol, e.g., ACTIPORE™ or other form of porous coated titanium or periapatite coated titanium.

In some embodiments, implantation of the implantable device may be achieved step-wise in multiple stages. For example, the implantable device may be constructed to be implanted at an initial stage to establish primary fixation, then at a subsequent stage additional implantation or assembly can be performed to add increased pull-out strength and other reinforcing properties to the fully assembled implantable device.

Other forms of implantable devices and variations of the implantable device are also disclosed in co-pending and co-owned U.S. patent application Ser. No. 12/950,306, filed Nov. 19, 2010 and entitled "IMPLANTABLE DEVICES FOR SUBCHONDRAL TREATMENT OF JOINT PAIN," U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitle "BONE-DERIVED IMPLANTABLE DEVICES FOR SUBCHONDRAL TREATMENT OF JOINT PAIN," the contents of which are herein incorporated in their entirety by reference.

While each of the above-mentioned treatment modalities may be administered independent of one another, it is contemplated that any combination of these modalities may be applied together and in any order so desired, depending on the severity of the OA or DDD.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A method of reinforcing bone located in a targeted bone marrow lesion (BML) in a subchondral region of a vertebral body for treating the targeted bone marrow lesion, the method comprising:
   identifying a bone marrow lesion in a subchondral region of a vertebral body so as to establish a targeted bone marrow lesion for receiving treatment, the vertebral body including a superior vertebral endplate with a superior articular surface and an inferior vertebral endplate with an inferior articular surface, wherein said identifying includes identifying with MRI;
   creating, in the vertebral body that contains the targeted bone marrow lesion in the subchondral region, a subchondral injection path to an area in or adjacent to the targeted bone marrow lesion for injecting an injectable bone filling material into said area for reinforcing bone located in the targeted bone marrow lesion, wherein said creating preserves an existing condition of the superior articular surface of the vertebral body and an existing condition of the inferior articular surface of the vertebral body, and is conducted without further creating a void in or adjacent to the targeted bone marrow lesion; and
   injecting an injectable bone filling material into said area via the subchondral injection path, wherein the injectable bone filling material is left in the area for hardening in the area so as to reinforce bone located in the targeted bone marrow lesion, wherein the injectable bone filling material is left in the area without also delivering a structural implant device to the area in addition to the injectable bone filling material.

2. The method of claim 1, wherein the injectable bone filling material includes a calcium phosphate.

3. The method of claim 1, wherein said creating is performed percutaneously.

4. The method of claim 1, wherein said creating is performed arthroscopically.

5. The method of claim 1, wherein the subchondral region occurs in a facet.

6. The method of claim 1, wherein the subchondral injection path is created with a needle.

7. The method of claim 1, wherein said area is in the targeted bone marrow lesion.

8. A method of reinforcing bone located in a targeted bone marrow lesion (BML) in a subchondral region of a vertebral body for treating the targeted bone marrow lesion, the method comprising:

identifying a bone marrow lesion in a subchondral region of a vertebral body so as to establish a targeted bone marrow lesion for receiving treatment, the vertebral body including a superior vertebral endplate with a superior articular surface and an inferior vertebral endplate with an inferior articular surface, wherein said identifying includes identifying with MRI;

creating, in the vertebral body that contains the targeted bone marrow lesion in the subchondral region, a subchondral injection path to an area in or adjacent to the targeted bone marrow lesion for injecting an injectable bone filling material into said area for reinforcing bone located in the targeted bone marrow lesion, wherein said creating preserves an existing condition of the superior articular surface of the vertebral body and an existing condition of the inferior articular surface of the vertebral body, and is conducted without further creating a void in or adjacent to the targeted bone marrow lesion; and injecting an injectable bone filling material into said area via the subchondral injection path, wherein the injectable bone filling material is left in the area for hardening in the area so as to reinforce bone located in the targeted bone marrow lesion, wherein the injectable bone filling material is left in the area without also delivering a structural implant device to the area in addition to the injectable bone filling material, wherein the injectable bone filling material envelopes the targeted bone marrow lesion.

9. The method of claim 8, wherein the injectable bone filling material includes a calcium phosphate.

10. The method of claim 8, wherein said creating is performed percutaneously.

11. The method of claim 8, wherein said creating is performed arthroscopically.

12. The method of claim 8, wherein the subchondral region occurs in a facet.

13. The method of claim 8, wherein the subchondral injection path is created with a needle.

14. The method of claim 8, wherein said area is in the targeted bone marrow lesion.

* * * * *